US012584106B2

(12) United States Patent
Ishikawa et al.

(10) Patent No.: US 12,584,106 B2
(45) Date of Patent: Mar. 24, 2026

(54) METHOD FOR PRODUCING OLIGODENDROCYTE-LIKE CELLS

(71) Applicants: JSR CORPORATION, Tokyo (JP); KEIO UNIVERSITY, Tokyo (JP)

(72) Inventors: Mitsuru Ishikawa, Tokyo (JP); Hideyuki Okano, Tokyo (JP)

(73) Assignees: JSR CORPORATION, Tokyo (JP); KEIO UNIVERSITY, Tokyo (JP)

( * ) Notice: Subject to any disclaimer, the term of this patent is extended or adjusted under 35 U.S.C. 154(b) by 504 days.

(21) Appl. No.: 18/116,415

(22) Filed: Mar. 2, 2023

(65) Prior Publication Data

US 2023/0203439 A1 Jun. 29, 2023

Related U.S. Application Data

(63) Continuation of application No. PCT/JP2021/033098, filed on Sep. 9, 2021.

(30) Foreign Application Priority Data

Sep. 10, 2020 (JP) ................................. 2020-152305

(51) Int. Cl.
 *C12N 5/079* (2010.01)
 *C12N 15/86* (2006.01)
(52) U.S. Cl.
 CPC ........... *C12N 5/0622* (2013.01); *C12N 15/86* (2013.01); *C12N 2501/60* (2013.01); *C12N 2506/45* (2013.01); *C12N 2740/15043* (2013.01)

(58) Field of Classification Search
 CPC .................................................... C12N 5/0622
 See application file for complete search history.

(56) References Cited

U.S. PATENT DOCUMENTS

2016/0029604 A1* 2/2016 Fahrenkrug ........ A01K 67/0275
 800/15
2019/0322981 A1 10/2019 Ehrlich et al.
 (Continued)

FOREIGN PATENT DOCUMENTS

JP 2020501533 A 1/2020
JP 2020526212 A 8/2020
 (Continued)

OTHER PUBLICATIONS

P. Li, (2015), Science China Life Sciences, vol. 59, No. 11, pp. 1131-1138 (Year: 2015).*
 (Continued)

*Primary Examiner* — Mark L Shibuya
(74) *Attorney, Agent, or Firm* — Element IP, PLC

(57) ABSTRACT
A method is provided for producing oligodendrocyte-like cells, including (A) increasing abundances of oligodendrocyte transcription factor 2 (OLIG2) mutant and SRY-box transcription factor 10 (SOX10) in human pluripotent stem cells and (B) culturing the human pluripotent stem cells in which the abundances of the OLIG2 mutant and the SOX10 are increased and consequently differentiating the human pluripotent stem cells into oligodendrocyte-like cells, in which the OLIG2 mutant lacks a serine residue of wild-type OLIG2 at position 147, or the serine residue of the wild-type OLIG2 at position 147 is substituted with an amino acid other than serine.

9 Claims, 4 Drawing Sheets

(56) References Cited

U.S. PATENT DOCUMENTS

| | | |
|---|---|---|
| 2020/0018746 A1 | 1/2020 | Tekin et al. |
| 2020/0048604 A1 | 2/2020 | Goldman et al. |

FOREIGN PATENT DOCUMENTS

| | | |
|---|---|---|
| WO | WO-2018096343 A1 | 5/2018 |
| WO | WO-2019014553 A1 | 1/2019 |

OTHER PUBLICATIONS

H. Li, (2011), Neuron, vol. 69, pp. 918-929 (Year: 2011).*

Ligon 2007 Neuron, vol. 53, pp. 503-517 (Year: 2007).*

Liu Jul. 6, 2021, Neurochemical Research, vol. 46, pp. 2776 to 2782 (Year: 2021).*

Sun 2011, Neuron, vol. 69, pp. 906-917 (Year: 2011).*

Elbaz B. et al., "Molecular Control of Oligodendrocyte Development", Trends in Neurosciences., 2019, vol. 42(4), pp. 263-277.

Garcia-Leon J. A., et al., "SOX10 Single Transcription Factor-Based Fast and Efficient Generation of Oligodendrocytes from Human Pluripotent Stem Cells", Stem Cell Reports, 10(2), 655-672, 2018.

Hu, B. Y., et al., "Human oligodendrocytes from embryonic stem cells: conserved SHH signaling networks and divergent FGF effects", Development, 136(9), 1443-1452, 2009.

International Search Report issued Nov. 22, 2021 in PCT/JP2021/033098 (with English translation), 6 pages.

Li H. et al., Phosphorylation regulates OLIG2 cofactor choice and the motor neuron-oligodendrocyte fate switch, Neuron, 2011, vol. 69(5), pp. 918-929.

Zhang M. et al., "Chapter11, Gene Delivery and Expression Systems in Induced Pluripotent Stem Cells", Interface Oral Health Science 2016 [online], 2017, pp. 121-133, URL: https://link.springer.com/chapter/10.1007/978-981-10-1560-1_11, [retrieved on Nov. 10, 2021].

Ehrlich, Marc, et al., "Rapid and efficient generation of oligodendrocytes from human induced pluripotent stem cells using transcription factors", Proceedings of the National Academy of Sciences, vol. 114, No. 11, Feb. 28, 2017, p. E2243-E2252.

Extended European Search Report issued Sep. 24, 2024 in corresponding European Patent Application No. 21866814.3, 11 pages.

Li, Pengyan, et al., "Accelerated generation of oligodendrocyte progenitor cells from human induced pluripotent stem cells by forced expression of Sox10 and Olig2", Science China Life Sciences, Zhongguo Kexue Zazhishe, China, vol. 59, No. 11, Oct. 25, 2016, pp. 1131-1138.

* cited by examiner

METHOD FOR PRODUCING OLIGODENDROCYTE-LIKE CELLS

BACKGROUND OF THE INVENTION

Field of the Invention

The present invention relates to a method for producing oligodendrocyte-like cells. More specifically, the present invention relates to a method for producing oligodendrocyte-like cells, oligodendrocyte-like cells, and a co-culture of oligodendrocyte-like cells and nerve-like cells. Priority is claimed on Japanese Patent Application No. 2020-152305, filed Sep. 10, 2020, the content of which is incorporated herein by reference.

Description of Related Art

There is a demand for using nervous system tissues for basic research, elucidation of nervous system diseases, and the like. However, experimental results obtained using nervous system tissues of experimental animals such as mice and rats may have problems in terms of extrapolation to humans, and there are limitations on the use of human nervous system tissues. For this reason, the in vitro formation and use of human nervous system tissue have been examined.

However, it is known that brain organoids produced from pluripotent stem cells such as induced pluripotent stem (iPS) cells are mainly composed of nerve cells and neural stem cells and do not include fully mature glial cells (astrocytes, oligodendrocytes, microglia, and the like).

It has been revealed that glial cells are responsible for the survival and exhibition of functions of nerve cells, such as the supply of nutrients to nerve cells, and not only nerve cells but also glial cells play an important role in the exhibition of brain function. As a result, there is a need for techniques to generate glial cells in vitro.

For example, Non-Patent Document 1 describes that human iPS cells have been induced to differentiate into oligodendrocyte-like cells by expressing an SRY-box transcription factor 10 (SOX10) gene.

In addition, Non-Patent Document 2 describes that the expression of OLIG2 is necessary for the differentiation of human ES cells into oligodendrocyte-like cells.

CITATION LIST

Non-Patent Documents

Non-Patent Document 1

Garcia-Leon J. A., et al., SOX10 Single Transcription Factor-Based Fast and Efficient Generation of Oligodendrocytes from Human Pluripotent Stem Cells, Stem Cell Reports, 10(2), 655-672, 2018

Non-Patent Document 2

Hu, B. Y., et al., Human oligodendrocytes from embryonic stem cells: conserved SHH signaling networks and divergent FGF effects, Development, 136(9), 1443-1452, 2009.

SUMMARY OF INVENTION

Technical Problem

However, the inventors found that in the case where iPS cells are induced to differentiate into oligodendrocyte-like cells by the method described in Non-Patent Document 1, there is a large difference in differentiation induction efficiency between iPS cell lines, and the differentiation is induced not only to oligodendrocyte-like cells but also to astrocyte-like cells. In addition, according to the method described in Non-Patent Document 2, the differentiation is induced not only to oligodendrocyte-like cells but also motor nerve cells. An object of the present invention is to provide a technique for efficiently producing oligodendrocyte-like cells in vitro.

Solution to Problem

The present invention includes the following aspects.

[1] A method for producing oligodendrocyte-like cells, including: a step (A) of increasing abundances of oligodendrocyte transcription factor 2 (OLIG2) mutant and SRY-box transcription factor 10 (SOX10) in human pluripotent stem cells; and a step (B) of culturing the human pluripotent stem cells in which the abundances of the OLIG2 mutant and the SOX10 are increased and consequently differentiating the human pluripotent stem cells into oligodendrocyte-like cells, in which the OLIG2 mutant lacks a serine residue of wild-type OLIG2 at position 147, or the serine residue of the wild-type OLIG2 at position 147 is substituted with an amino acid other than serine.

[2] The method for producing oligodendrocyte-like cells according to [1], in which the step (A) is carried out by introducing vectors containing nucleic acids encoding the OLIG2 mutant and the SOX10 into the human pluripotent stem cells.

[3] The method for producing oligodendrocyte-like cells according to [1], in which the step (A) is carried out by adding or removing a tetracycline-based antibiotic to or from a culture medium of the human pluripotent stem cells into which vectors containing nucleic acids encoding the OLIG2 mutant and the SOX10 under regulation of a tetracycline response element are introduced.

[4] The method for producing oligodendrocyte-like cells according to [2] or [3], in which the vectors containing the nucleic acids encoding the OLIG2 mutant and the SOX10 consist of a combination of a vector containing a nucleic acid encoding the OLIG2 mutant and a vector containing a nucleic acid encoding the SOX10.

[5] The method for producing oligodendrocyte-like cells according to [4], in which the vector containing the nucleic acid encoding the OLIG2 mutant is a transposon vector.

[6] The method for producing oligodendrocyte-like cells according to [4] or [5], in which the vector containing the nucleic acid encoding the SOX10 is a lentivirus vector.

[7] The method for producing oligodendrocyte-like cells according to any one of [1] to [6], in which the human pluripotent stem cells are human induced pluripotent stem cells.

[8] Oligodendrocyte-like cells that are produced by the production method according to any one of [1] to [7].

[9] A co-culture of the oligodendrocyte-like cells according to [8] and nerve-like cells.

It can also be said that the present invention includes the following aspects.

[P1] A method for producing oligodendrocytes, including: a step (A) of increasing abundances of oligodendrocyte transcription factor 2 (OLIG2) mutant and SRY-box transcription factor 10 (SOX10) in human pluripotent stem cells; and a step (B) of culturing the human pluripotent stem cells in which the abundances of the OLIG2 mutant and the SOX10 are increased and consequently differentiating the human pluripotent stem cells into oligodendrocytes, in which the OLIG2 mutant lacks a serine residue of wild-type OLIG2 at position 147, or the serine residue of the wild-type OLIG2 at position 147 is substituted with an amino acid other than serine.

[P2] The method for producing oligodendrocytes according to [P1], in which the step (A) is carried out by introducing vectors containing nucleic acids consisting of base sequences encoding the OLIG2 mutant and the SOX10 into the human pluripotent stem cells.

[P3] The method for producing oligodendrocytes according to [P1], in which the step (A) is carried out by adding or removing a tetracycline-based antibiotic to or from a culture medium of the human pluripotent stem cells into which vectors containing nucleic acids consisting of base sequences encoding the OLIG2 mutant and the SOX10 under regulation of a tetracycline response element are introduced.

[P4] The method for producing oligodendrocytes according to [P2] or [P3], in which the vectors containing the nucleic acids consisting of base sequences encoding the OLIG2 mutant and the SOX10 consist of a combination of a vector containing a nucleic acid consisting of a base sequence encoding the OLIG2 mutant and a vector containing a nucleic acid consisting of a base sequence encoding the SOX10.

[p5] The method for producing oligodendrocytes according to [P4], in which the vector containing the nucleic acid consisting of a base sequence encoding the OLIG2 mutant is a transposon vector.

[P6] The method for producing oligodendrocytes according to [P4] or [P5], in which the vector containing the nucleic acid consisting of a base sequence encoding the SOX10 is a lentivirus vector.

[P7] The method for producing oligodendrocytes according to any one of [P1] to [P6], in which the human pluripotent stem cells are human induced pluripotent stem cells.

[P8] Oligodendrocytes that are produced by the production method according to any one of [P1] to [P7].

[P9] A co-culture of the oligodendrocytes according to [P8] and nerve cells.

[P10] Human pluripotent stem cells for producing oligodendrocytes, into which nucleic acids consisting of base sequences encoding an OLIG2 mutant and SOX10 are introduced, where the OLIG2 mutant lacks a serine residue of wild-type OLIG2 at position 147, or the serine residue of the wild-type OLIG2 at position 147 is substituted with an amino acid other than serine.

[P11] The human pluripotent stem cells for producing oligodendrocytes according to [P10], into which the nucleic acid consisting of the base sequences encoding the OLIG2 mutant and the SOX10 under regulation of a tetracycline response element are introduced.

Advantageous Effects of Invention

According to the present invention, it is possible to provide a technique for efficiently producing oligodendrocyte-like cells in vitro.

DETAILED DESCRIPTION OF THE INVENTION

Method for Producing Oligodendrocyte-like Cells

Figure 1A:
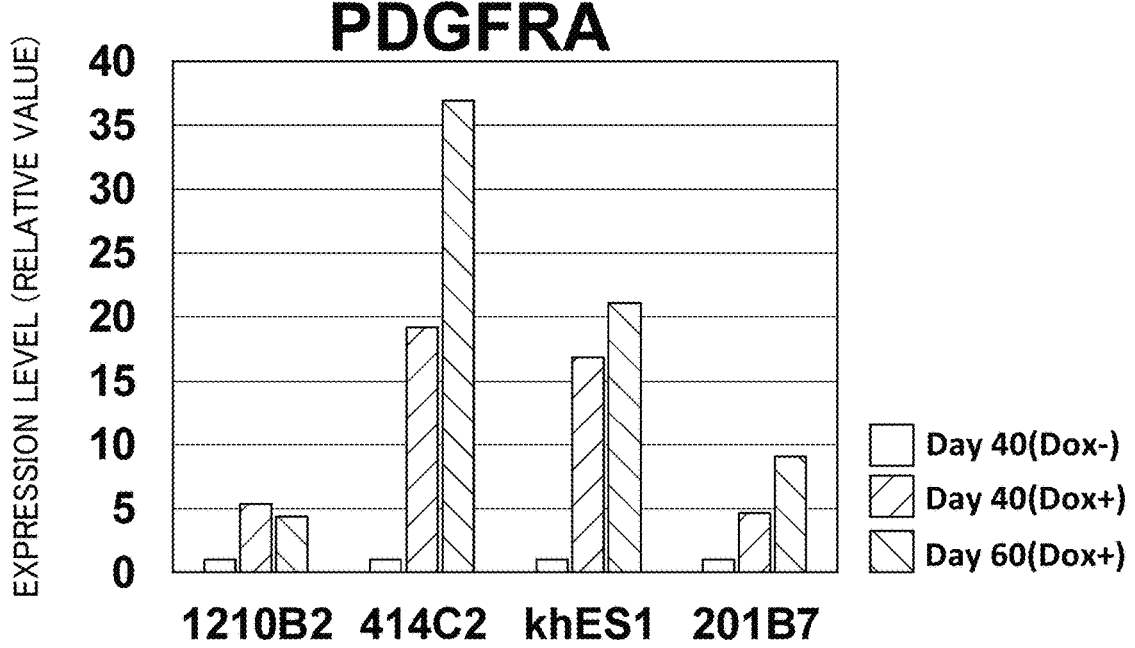
FIG. 1A shows a graph of the result of quantitative RT-PCR in Experimental Example 1.

In one embodiment, the present invention provides a method for producing oligodendrocyte-like cells, including a step (A) of increasing abundances of an OLIG2 mutant and SOX10 in human pluripotent stem cells and a step (B) of culturing the human pluripotent stem cells in which the abundances of the OLIG2 mutant and the SOX10 are increased and consequently differentiating the human pluripotent stem cells into oligodendrocyte-like cells, in which the OLIG2 mutant lacks a serine residue of the wild-type OLIG2 at position 147, or the serine residue of the wild-type OLIG2 at position 147 is substituted with an amino acid other than serine.

In the present specification, an oligodendrocyte-like cell means a cell that is functionally and morphologically equivalent to an oligodendrocyte in vivo and thus can also be referred to as the oligodendrocyte. The oligodendrocyte-like cell expresses oligodendrocyte markers described below.

As will be described later in Examples, according to the production method of the present embodiment, oligodendrocyte-like cells can be efficiently produced in a short period of time. For example, 10 days after increasing the abundance of the OLIG2 mutant and SOX10 in human pluripotent stem cells, cells that exhibit a morphology characteristic of oligodendrocytes can be obtained under microscopic observation.

The fact that the efficiency of differentiation into oligodendrocyte-like cells is high means that the expression level of an oligodendrocyte marker is high compared to a control, that the expression levels of a neural stem cell marker, a nerve cell marker, and astrocyte marker are low compared with a control, and that there is little variation in differentiation induction efficiency among human pluripotent stem cell lines.

Examples of the oligodendrocyte markers include platelet derived growth factor receptor alpha (PDGFRA), proteolipid protein 1 (PLP1), and 2',3'-cyclic nucleotide 3' phosphodiesterase (CNP).

Examples of the neural stem cell marker include sex determining region Y (SRY)-box 2 (SOX2) and paired box 6 (PAX6).

Examples of the nerve cell marker include microtubule-associated protein 2 (MAP2), synapsin 1 (SYN1), and βIII-tubulin (TUBB3).

Examples of the astrocyte marker include glial fibrillary acidic protein (GFAP) and S100 calcium binding protein B (S100β).

Examples of the control include cells in which the abundance of SOX10 alone has been increased, cells in which the abundance of wild-type OLIG2 alone has been increased, and cells in which the abundance of wild-type OLIG2 and SOX10 has been increased.

As will be described later in Examples, in the oligodendrocyte-like cells obtained by the method of the present embodiment, in which the abundances of the OLIG2 mutant and SOX10 are increased, the expression level of the oligodendrocyte marker is as high as about 3 to 5 times as compared with the case where the abundance of SOX10 alone is increased. In addition, the expression level of the astrocyte marker is reduced to about ½ to ⅕. In addition, the variation in the differentiation induction efficiency among human pluripotent stein cell lines is also reduced.

In the step (A), the abundance of the OLIG2 mutant and SOX10 is increased in human pluripotent stem cells. Here, increasing the abundance may be, for example, introducing the OLIG2 mutant and SOX10 into cells in the form of protein. Alternatively, it may be introducing the OLIG2 mutant and SOX10 into cells in the form of mRNA. Alternatively, it may be introducing, into cells, expression vectors that forcibly express a gene encoding the OLIG2 mutant (a nucleic acid consisting of a base sequence encoding the OLIG2 mutant) and a gene encoding SOX10 (a nucleic acid consisting of a base sequence encoding SOX10). Alternatively, cells into which an expression vector capable of regulating the expression of the gene encoding the OLIG2 mutant and the gene encoding SOX10 has been introduced may be prepared, and then the expression thereof may be induced to increase the abundance of the OLIG2 mutant and SOX10.

Here, the vector containing the nucleic acids encoding the OLIG2 mutant and SOX10 may contain the nucleic acid encoding the OLIG2 mutant and the nucleic acid encoding SOX10 in a single vector or may be composed of a combination of a plurality of vectors of a vector containing the nucleic acid encoding the OLIG2 mutant and a vector containing the nucleic acid encoding SOX10.

The introduction of proteins, mRNAs, and expression vectors can be carried out by general methods as necessary, examples of which include electroporation, lipofection, and microinjection.

The expression vector may be a plasmid vector, may be a transposon vector, or may be a virus vector, or a combination thereof may be used.

The transposon vector may be such that it can be completely removed from cells as necessary. Examples of such a transposon vector include a PiggyBac vector.

Examples of the virus vector include a retrovirus vector, a lentivirus vector, an adeno-associated virus vector, and an adenovirus vector. In the case where the expression vector is a virus vector, it can be introduced into cells by infection.

For example, as will be described later in the Examples, the vector containing the nucleic acid encoding the OLIG2 mutant may be a transposon vector. In addition, the vector containing the nucleic acid encoding SOX10 may also be a lentivirus vector.

Examples of the expression vector capable of regulating expression include those capable of regulating expression in response to external stimuli. Such expression vectors include at least a promoter capable of inducing the expression of a downstream gene in response to an external stimulus, and the OLIG2 mutant gene and the SOX10 gene, the expression of which is regulated by the promoter.

The promoter is not particularly limited as long as it can regulate the expression of the downstream gene in response to an external stimulus, and examples thereof include a promoter having a tetracycline response element (TRE) in the case where the external stimulus is the presence or absence of a tetracycline-based antibiotic.

In this case, the step (A) is carried out by adding or removing a tetracycline-based antibiotic to or from a culture medium of the human pluripotent stem cells into which vectors containing the nucleic acids encoding the OLIG2 mutant and SOX10 under the regulation of the tetracycline response element are introduced.

In the case where the external stimulus is the presence of the tetracycline-based antibiotic (a Tet-On system), the expression of the downstream gene can be induced by binding a complex of a tetracycline-based antibiotic and a reverse tetracycline-controlled transactivator (rtTA) to TRE.

On the other hand, in the case where the external stimulus is the absence of a tetracycline-based antibiotic (a Tet-Off system), the expression of the downstream gene can be induced by binding a tetracycline-controlled transactivator (tTA) to TRE. In this case, in the presence of the tetracycline-based antibiotic, the tetracycline-based antibiotic forms a complex with tTA, which makes it impossible for tTA to bind to TRE, whereby the expression of the downstream gene is suppressed.

Examples of the tetracycline-based antibiotic include tetracycline derivatives such as tetracycline and doxycycline. In the case where doxycycline is used as the tetracycline-based antibiotic, the concentration of the doxycycline to be added to the culture medium can be 0.1 to 10 μg/mL, where 1 to 2 μg/mL is more preferable.

In addition, in the case where the external stimulus is the presence of an ecdysteroid, examples of the promoter include a promoter that can induce the expression of the downstream gene by the binding of the ecdysteroid to an ecdysone receptor-retinoid receptor complex. The ecdysteroid includes ecdysone, muristerone A, ponasterone A, and the like.

In addition, in the case where the external stimulus is the presence of FKCsA, examples of the promoter include a promoter that can induce the expression of the downstream gene by the binding of FKCsA to a complex of a Ga14 DNA-binding domain fused to FKBP12 and a VP16 activator domain fused to cyclophilin.

The expression vector may contain an enhancer, a silencer, a drug selection marker, a replication origin, and the like, as necessary. Examples of the drug selection markers include a hygromycin resistance gene, a puromycin resistance gene, and a neomycin resistance gene.

The NCBI accession number of the wild-type human OLIG2 protein is NP_005797.1 or the like. The NCBI accession number of the wild-type human OLIG2 cDNA is NM_005806.4 or the like.

It is known that OLIG2 forms a homodimer in the case where a serine residue of the wild-type human OLIG2 at position 147 is phosphorylated. The OLIG2 mutant that is used in the production method of the present embodiment may be any human OLIG2 that does not form a homodimer, which may be one that lacks the serine residue of the wild-type OLIG2 at position 147 or may be one in which the serine residue of the wild-type OLIG2 at position 147 is substituted with an amino acid residue other than the serine residue. The amino acid residue other than the serine residue is preferably the alanine residue.

As will be described later in Examples, the inventors found that in the case of increasing the expression levels of the OLIG2 mutant together with SOX10 in human pluripotent stem cells, it is possible to efficiently produce oligodendrocyte-like cells in a short period of time, thereby completing the present invention.

The NCBI accession number of the human SOX10 protein is NP_008872.1 or the like. The NCBI accession number of the human SOX10 cDNA is NM_006941.4 or the like.

The OLIG2 mutant may have a mutation as long as it has the activity of inducing the differentiation of human pluripotent stem cells into oligodendrocyte-like cells. In the case where the OLIG2 mutant further has a mutation in addition to the mutation that lacks the serine residue of the wild-type OLIG2 at position of 147 or the mutation in which the serine residue of the wild-type OLIG2 at position of 147 is substituted with an amino acid other than serine, it preferably has 80% or more sequence identity, preferably has 90% or more sequence identity, and still more preferably has 95% or more sequence identity with the wild-type protein or cDNA identified by the NCBI accession number described above.

In addition, SOX10 may have a mutation as long as it has the activity of inducing the differentiation of human pluripotent stem cells into oligodendrocyte-like cells. In the case where SOX10 has a mutation, it preferably has 80% or more sequence identity, preferably has 90% or more sequence identity, and still more preferably has 95% or more sequence identity with the wild-type protein or cDNA identified by the NCBI accession number described above.

Here, the sequence identity of an amino acid sequence is a value indicating a ratio of matching between an amino acid sequence of interest (a target amino acid sequence) and an amino acid sequence as a reference (a reference amino acid sequence). The sequence identity of the target amino acid sequence with respect to the reference amino acid sequence can be determined, for example, as follows. First, a reference amino acid sequence and a target amino acid sequence are aligned. Here, each amino acid sequence may contain gaps to maximize sequence identity. Subsequently, the number of matching amino acids in the reference amino acid sequence and the target amino acid sequence is calculated, and the sequence identity can be determined according to Expression (F1).

$$\text{Sequence identity (\%)} = \text{number of matching amino acids/total number of amino acids in target amino acid sequence} \times 100 \quad (F1)$$

Similarly, the sequence identity of the target base sequence with respect to the reference base sequence can be determined, for example, as follows. First, a reference base sequence and a target base sequence are aligned. Here, each base sequence may contain gaps to maximize sequence identity. Subsequently, the number of matching bases in the reference base sequence and the target base sequence is calculated, and the sequence identity can be determined according to Formula (F2).

$$\text{Sequence identity (\%)} = \text{number of matching bases/total number of bases in target base sequence} \times 100 \quad (F2)$$

In the production method of the present embodiment, examples of the pluripotent stem cell include an embryonic stem cell (an ES cell) and an induced pluripotent stem cell (an iPS cell). In addition, the pluripotent stem cells may be cells derived from a healthy subject or may be cells derived from neurological disease patients. In the case where oligodendrocyte-like cells are produced from pluripotent stem cells derived from neurological disease patients, the obtained oligodendrocyte-like cells can be used as a model of the neurological disease. Such oligodendrocyte-like cells are useful for elucidating the mechanism of the neurological disease.

Subsequently, in the step (B), the human pluripotent stem cells in which the abundance of the OLIG2 mutant and SOX10 has been increased are cultured. As a result, the human pluripotent stem cells differentiate into oligodendrocyte-like cells.

The production method of the present embodiment may have a step of differentiating human pluripotent stem cells into neural stem cells, or may not have a step of differentiating human pluripotent stem cells into neural stem cells but be a method of directly inducing the differentiation of human pluripotent stem cells into oligodendrocyte-like cells.

In the case where the production method of the present embodiment has a step of differentiating human pluripotent stem cells into neural stem cells, the human pluripotent stem cells may be first induced to differentiate into neural stem cells, and then, the step (A) of increasing the abundance of the OLIG2 mutant and SOX10 in the cells induced to differentiate into neural stein cells and the step (B) of culturing the cells, in which the abundance of the OLIG2 mutant and SOX10 has been increased, and consequently differentiating the cells into oligodendrocyte-like cells may be carried out.

As the step of differentiating human pluripotent stem cells into neural stem cells, a generally used method can be appropriately adopted. Examples thereof include a method of culturing human pluripotent stem cells in the presence of fibroblast growth factor 2 (FGF2), a Rho-associated protein kinase (ROCK) signal transduction pathway inhibitor, and a leukemia inhibitory factor (LIF).

Examples of the ROCK signal transduction pathway inhibitor include Y-27632 (CAS number: 129830-38-2), Fasudil/HA1077 (CAS number: 105628-07-7), H-1152 (CAS number: 871543-07-6), Wf-536 (CAS number: 539857-64-2), and derivatives thereof.

The final concentration of the ROCK signal transduction pathway inhibitor in the culture medium is generally 0.1 μM to 100 μM, preferably 5 μM to 50 μM, and more preferably 10 μM to 30 μM.

Oligodendrocyte-like Cells

In one embodiment, the present invention provides oligodendrocyte-like cells produced by the production method described above. Since the oligodendrocyte-like cells of the present embodiment can be efficiently produced in vitro, they can be suitably used for basic research, elucidation of nervous system diseases, and the like.

The gene encoding the OLIG2 mutant and a gene encoding exogenous SOX10 may be introduced into the genome of the oligodendrocyte-like cell of the present embodiment.

Co-Culture

In one embodiment, the present invention provides a co-culture of the above-described oligodendrocyte-like cells and neuronal-like cells.

In the present specification, the nerve-like cell means a cell that is functionally and morphologically equivalent to a nerve cell in vivo and thus can also be referred to as a nerve cell. The nerve-like cells express nerve cell markers described above.

As described above, the brain organoids produced from pluripotent stem cells are mainly composed of nerve cells and neural stem cells but do not contain fully mature glial cells. On the other hand, according to the co-culture of the present embodiment, a large amount of prepared oligodendrocyte-like cells and nerve-like cells can be co-cultured, which makes it possible to analyze the functions of nerve cells in a state close in vivo.

EXAMPLES

Next, the present invention will be described in more detail by showing experimental examples; however, the present invention is not limited to the experimental examples below.

Experimental Example 1

(Differentiation of iPS Cells into Oligodendrocyte-like Cells 1)

Human pluripotent stem cells were induced to differentiate into oligodendrocyte-like cells according to the method in the related art. Specifically, human pluripotent stem cells were made to express SOX10 and induced to differentiate into oligodendrocyte-like cells. As human pluripotent stem cells, iPS cell lines 1210B2, 414C2, and 201B7, and ES cell line khES1 were used.

First, a transposon vector (PiggyBac vector, Vector-Builder Inc.) was used to introduce a reverse tetracycline-controlled transactivator (rtTA3G, VectorBuilder Inc.) into human pluripotent stem cell lines (1210B2, 414C2, 201B7, khES1), and a gene-introduced line was obtained by drug selection. The hygromycin resistance gene was used as a drug selection marker for rtTA3G. An internal ribosome entry site (IRES) sequence was introduced between the rtTA3G and hygromycin resistance genes to bicistronically express these genes. HyPBase (VectorBuilder Inc.) was used as the transposase.

Each pluripotent stem cell was then dissociated into single cells and seeded. This point was designated as day 0. Subsequently, differentiation of each pluripotent stem cell line was induced by suspension culture in the presence of fibroblast growth factor 2 (FGF2), Rho-associated protein kinase (ROCK) signal transduction pathway inhibitor, and leukemia inhibitory factor (LIF). They formed neural stem cells and formed neurospheres, which are cell aggregates.

Subsequently, on the 14th day, the SOX10 gene under the regulation of a tetracycline response element was introduced into each neurosphere using a lentivirus vector (Vector-Builder Inc.). Cells were then dissociated and seeded on new Matrigel-coated plates for culture. Also, doxycycline was added to the culture medium to induce the expression of the SOX10 gene. As a culture medium, an oligodendrocyte progenitor differentiation-oriented glial cell production medium was used. For comparison, cells cultured without the addition of doxycycline were also prepared.

Subsequently, each cell was collected on days 40 and 60, and the expression levels of oligodendrocyte markers and astrocyte markers were quantified by quantitative RT-PCR. PDGFRA was used as an oligodendrocyte marker. GFAP was used as an astrocyte marker.

Figure 1B:
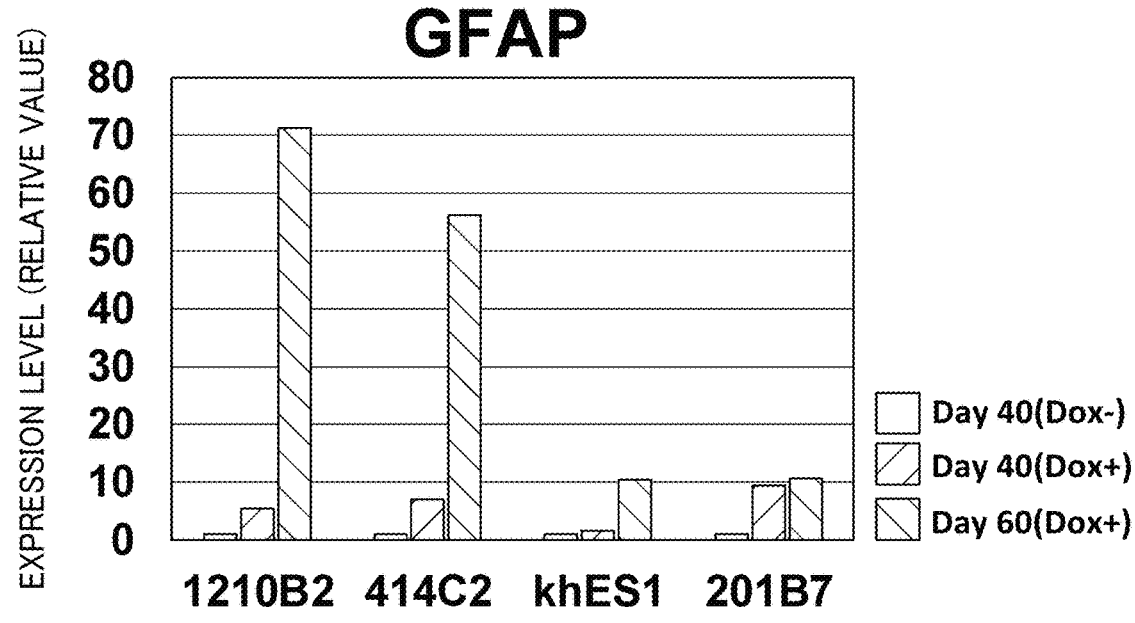
FIG. 1B shows a graph of the result of quantitative RT-PCR in Experimental Example 1.

FIG. 1A and FIG. 1B show graphs of the results of quantitative RT-PCR. FIG. 1A shows the result of quantifying the expression level of PDGFRA, and FIG. 1B shows the result of quantifying the expression level of GFAP. In FIG. 1A and FIG. 1B, "Day 40" indicates the results on the 40th day, "Day 60" indicates the results on the 60th day, "Dox−" indicates the results obtained without the addition of doxycycline, and "Dox+" indicates the results obtained with the addition of doxycycline.

As a result, as shown in FIG. 1A, it was confirmed that the addition of doxycycline to the culture medium induced the expression of oligodendrocyte markers. However, it was revealed that there is a large difference in the expression levels of oligodendrocyte markers among the pluripotent stem cell lines. In addition, as shown in FIG. 1B, an increase in the expression level of astrocyte markers was also confirmed. This result indicates that the induction of SOX10 gene expression induced the differentiation of not only oligodendrocyte-like cells but also astrocyte-like cells.

Experimental Example 2

(Differentiation of iPS Cells into Oligodendrocyte-like Cells 2)

OLIG2 mutants and SOX10 were expressed in human pluripotent stem cells and induced to differentiate into oligodendrocyte-like cells. As human pluripotent stem cells, iPS cell lines 1210B2, 414C2, and 201B7 were used.

Figure 2:
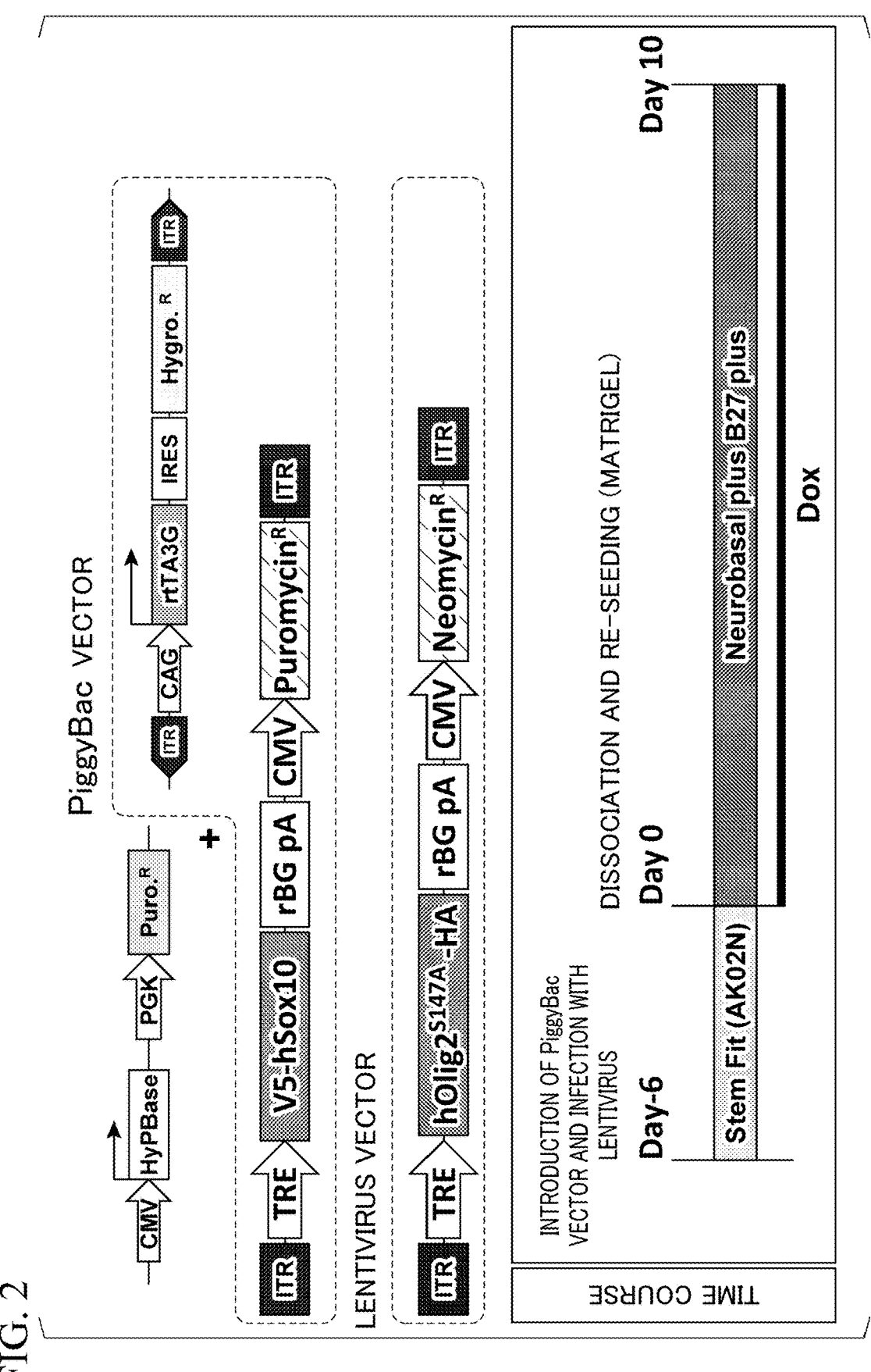
FIG. 2 shows a view of an outline of Experimental Example 2.

FIG. 2 is a diagram explaining the outline of the experiment. First, transposon vector (PiggyBac vector, Vector-Builder Inc.) was used to introduce the human SOX10 gene under the regulation of a reverse tetracycline-controlled transactivator (rtTA3G, VectorBuilder Inc.) and a tetracycline response element into each iPS cell. Then, a gene-introduced line was obtained by drug selection.

The hygromycin resistance gene was used as a drug selection marker for rtTA3G. The puromycin resistance gene was used as a drug selection marker for the human SOX10 gene. An internal ribosome entry site (IRES) sequence was introduced between the rtTA3G and hygromycin resistance genes to bicistronically express these genes. HyPBase (VectorBuilder Inc.) was used as the transposase.

Subsequently, using a lentivirus vector (VectorBuilder Inc.), a gene encoding an OLIG2 mutant under the regulation of a tetracycline response element was introduced into a cell line introduced with rtTA3G and SOX10, and a gene-introduced line was selected by drug selection. The neomycin resistance gene was used as a drug selection marker.

As the gene encoding the OLIG2 mutant, a gene encoding a mutant in which the serine residue of the wild-type OLIG2 at position 147 is mutated to an alanine residue (hereinafter sometimes referred to as "Olig2S147A") was used. A base sequence encoding an HA tag was added to the OLIG2 mutant.

For comparison, iPS cells into which no OLIG2 mutant was introduced were also prepared.

Subsequently, the obtained gene-introduced line was subjected to expansion culturing for 6 days. As the culture medium, a culture medium for pluripotent stem cell culturing (product name "Stem Fit (AK02N)", manufactured by Ajinomoto Co., Inc.) was used.

Cells were then dissociated and seeded onto new Matrigel-coated plates to induce differentiation into oligodendrocyte-like cells. In addition, doxycycline was added to the culture medium to induce the expression of the OLIG2 mutant and SOX10, or only SOX10. As a culture medium, a culture medium for nerve cell culturing was used. As a culture medium for pluripotent stem cell culturing, basal medium (product name "Neurobasal Plus Medium", Thermo Fisher Scientific, Inc.), 2% B27 supplement (Thermo Fisher Scientific, Inc.), 1% Glutamax (Thermo Fisher Scientific, Inc.) company), 1% CultureOne supplement (Thermo Fisher Scientific, Inc.), 200 μM ascorbic acid, 20 ng/mL brain-derived neurotrophic factor (BDNF), 20 ng/mL glial cell line-derived neurotrophic factor (GDNF), 20 ng/mL neuro-
trophin 3 (NT3), and 100 μM dibutyryl cyclic AMP (db-
cAMP) were used.

Experimental Example 3

(Examination by Immunochemical Staining)

Figure 3:
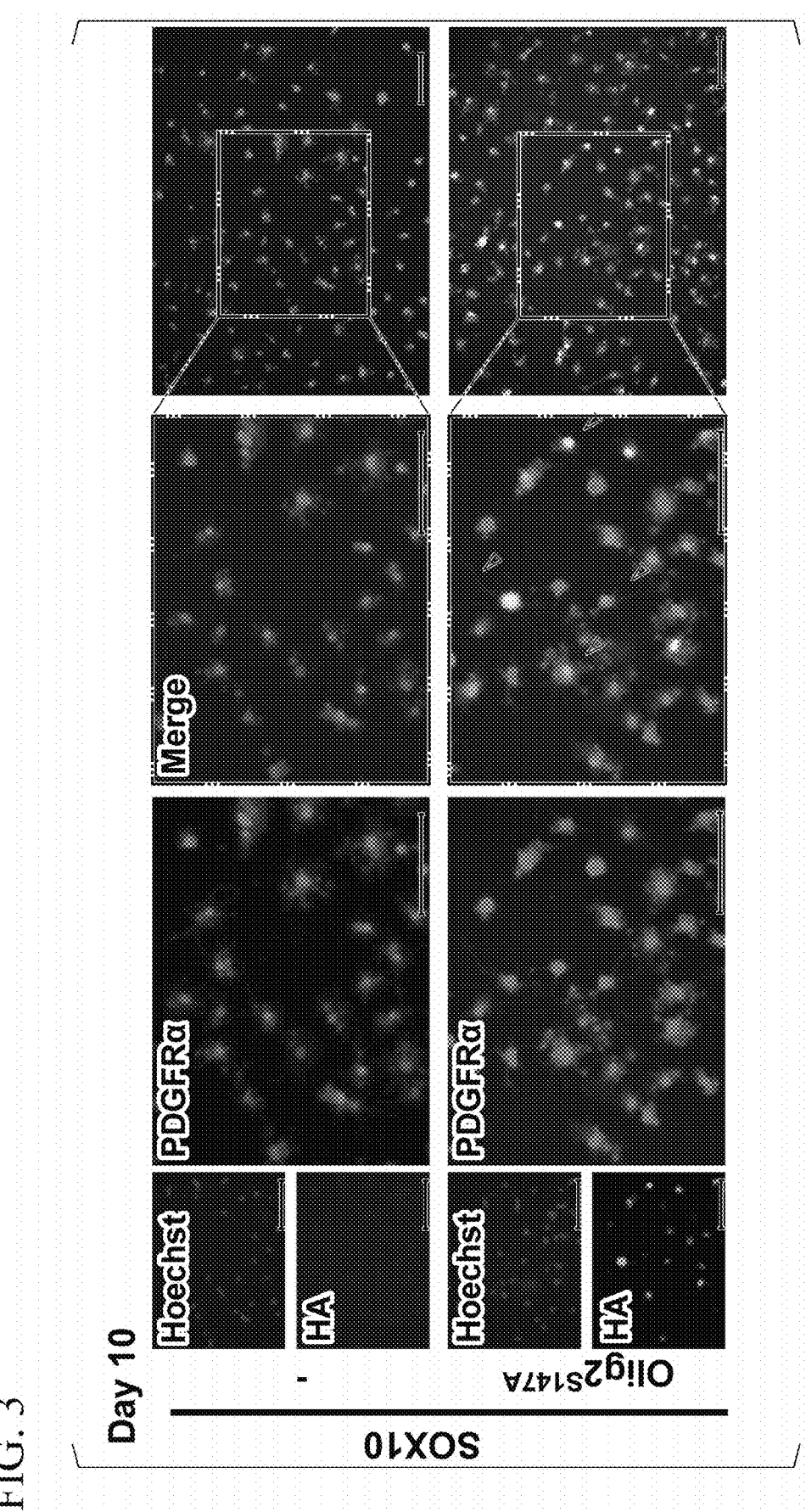
FIG. 3 shows fluorescence photomicrographic images of the results of Experimental Example 3.

The cells induced to differentiate into oligodendrocyte-
like cells in Experimental Example 2 were fixed and immu-
nochemically stained. FIG. 3 is a representative fluorescence
photomicrographic image showing the results of paraform-
aldehyde-fixing and immunochemical staining of the cells
(the 1210B2 line) cultured for 10 days in the presence of
doxycycline. These are representative results using the cul-
ture medium for nerve cell culturing as the culture medium.
The scale bar is 100 μm.

In FIG. 3, "Hoechst" is the result of staining the nucleus
with Hoechst 33342, "HA" is the result of staining the HA
tag with an anti-HA antibody, and "PDGFRα" indicates the
expression of the oligodendrocyte marker PDGFRA. It is the
result of detection with an anti-PDGFRα antibody, and
"Merge" is the result of combining photographic images in
which Hoechst 33342, HA, and PDGFRα were detected.

In addition, "SOX10" indicates the result of inducing the
expression of SOX10, "Olig2S147A" indicates the result of
inducing the expression of Olig2S147A, and "−" indicates
the result of not inducing the expression of Olig2S147A.
Arrowheads indicate the presence of protrusion-like struc-
tures characteristic of oligodendrocytes.

As a result, it became clear that in the case where the
OLIG2 mutant and SOX10 were expressed, the expression
level of the oligodendrocyte marker was increased compared
to the case where SOX10 was expressed alone, and mor-
phologically, the characteristics of oligodendrocytes were
more pronounced.

Experimental Example 4

(Examination by Quantitative RT-PCR)

The mRNAs of oligodendrocyte markers and astrocyte
markers in each cell cultured for 10 days in the presence of
doxycycline in Experimental Example 2 were quantified by
quantitative RT-PCR. PDGFRA was examined as an oligo-
dendrocyte marker. GFAP was also examined as an astrocyte
marker.

Figure 4A:
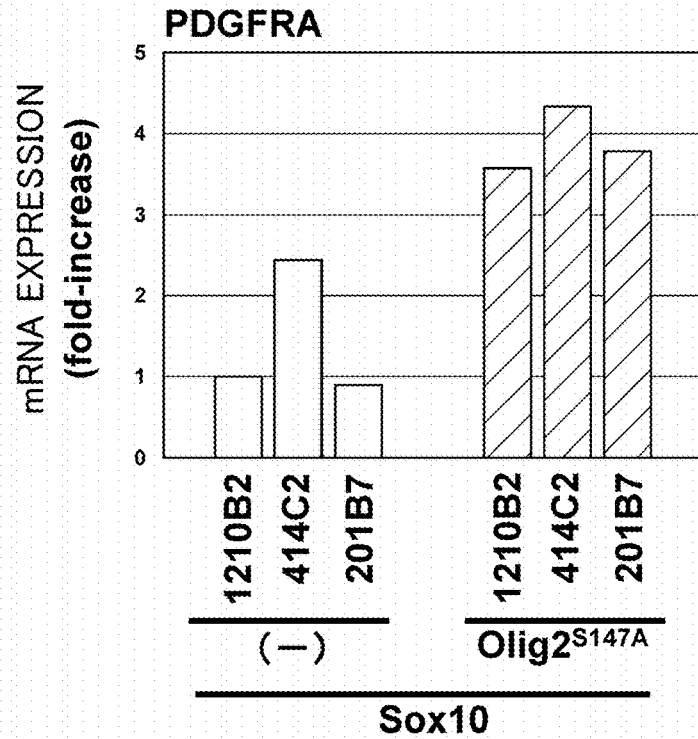
FIG. 4A shows a graph of the result of quantitative RT-PCR in Experimental Example 4.
Figure 4B:
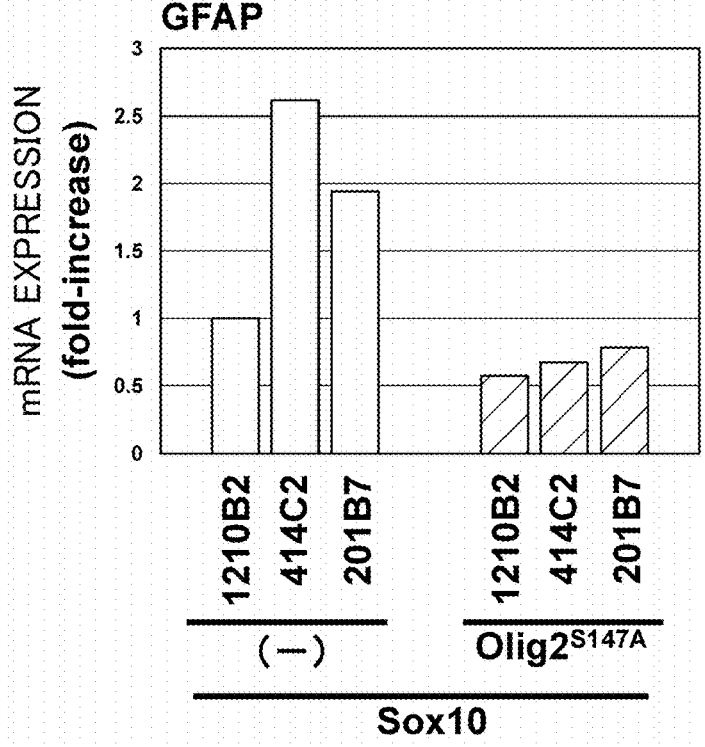
FIG. 4B shows a graph of the result of quantitative RT-PCR in Experimental Example 4.

FIG. 4A and FIG. 4B show graphs of the results of
quantitative RT-PCR. FIG. 4A shows the result of PDGFRA,
and FIG. 4B shows the result of GFAP. In FIG. 4A and FIG.
4B, the vertical axis indicates the mRNA expression level
(relative value). In addition, "SOX10" indicates the result of
inducing the expression of SOX10, "Olig2S147A" indicates
the result of inducing the expression of Olig2S147A, and
"(−)" indicates the result of not inducing the expression of
Olig2S147A.

As a result, it was revealed that in the case where the
OLIG2 mutant and SOX10 are expressed, the expression
level of the oligodendrocyte marker increases by about 3 to
5 times as compared with the case where SOX10 is
expressed alone, and the variation in the expression level
between cell lines is small.

In addition, it was revealed that in the case where the
OLIG2 mutant and SOX10 are expressed, the expression
level of the astrocyte marker is reduced to about ½ to ⅕ compared with the case where SOX10 is expressed alone,
and the variation in the expression level between cell lines
is small.

INDUSTRIAL APPLICABILITY

According to the present invention, it is possible to
provide a technique for efficiently producing oligodendro-
cyte-like cells in vitro.

What is claimed is:

1. A method for producing oligodendrocyte-like cells,
comprising:
    (A) increasing abundances of oligodendrocyte transcrip-
        tion factor 2 (OLIG2) mutant and SRY-box transcrip-
        tion factor 10 (SOX10) in human pluripotent stem
        cells; and
    (B) culturing the human pluripotent stem cells in which
        the abundances of the OLIG2 mutant and the SOX10
        are increased and consequently differentiating the
        human pluripotent stem cells into oligodendrocyte-like
        cells,
    wherein the OLIG2 mutant lacks a serine residue of
        wild-type OLIG2 at position 147, or the serine residue
        of the wild-type OLIG2 at position 147 is substituted
        with an amino acid other than serine.

2. The method for producing oligodendrocyte-like cells
according to claim 1,
    wherein (A) increasing is carried out by introducing
        vectors containing nucleic acids encoding the OLIG2
        mutant and the SOX10 into the human pluripotent stem
        cells.

3. The method for producing oligodendrocyte-like cells
according to claim 2,
    wherein the vectors containing the nucleic acids encoding
        the OLIG2 mutant and the SOX10 consist of a com-
        bination of a vector containing a nucleic acid encoding
        the OLIG2 mutant and a vector containing a nucleic
        acid encoding the SOX10.

4. The method for producing oligodendrocyte-like cells
according to claim 3,
    wherein the vector containing the nucleic acid encoding
        the OLIG2 mutant is a transposon vector.

5. The method for producing oligodendrocyte-like cells
according to claim 3,
    wherein the vector containing the nucleic acid encoding
        the SOX10 is a lentivirus vector.

6. The method for producing oligodendrocyte-like cells
according to claim 1,
    wherein (A) increasing is carried out by adding or remov-
        ing a tetracycline-based antibiotic to or from a culture
        medium of the human pluripotent stem cells into which
        vectors containing nucleic acids encoding the OLIG2
        mutant and the SOX10 under regulation of a tetracy-
        cline response element are introduced.

7. The method for producing oligodendrocyte-like cells
according to claim 1,
    wherein the human pluripotent stem cells are human
        induced pluripotent stem cells.

8. Oligodendrocyte-like cells that are produced by the
production method according to claim 1.

9. A co-culture of the oligodendrocyte-like cells according
to claim 8 and nerve-like cells.

* * * * *